United States Patent [19]

Fossel

[11] Patent Number: 5,895,658

[45] Date of Patent: Apr. 20, 1999

[54] TOPICAL DELIVERY OF L-ARGININE TO CAUSE TISSUE WARMING

[76] Inventor: Eric T. Fossel, 17 Sunset View Rd., S. Hero, Vt. 05486

[21] Appl. No.: 08/936,188

[22] Filed: Sep. 17, 1997

[51] Int. Cl.$^6$ .............................. A61K 6/00; A61K 7/00
[52] U.S. Cl. ............................. 424/401; 424/450
[58] Field of Search ..................... 424/401, 450

[56] References Cited

U.S. PATENT DOCUMENTS

| 4,681,897 | 7/1987 | Brand | 514/557 |
| 5,595,753 | 1/1997 | Hechtman | 424/440 |

OTHER PUBLICATIONS

Pauly et al., *Chemical Abstracts*, vol. 113, #65,069, 1990.
Riedel et al., *Chemical Abstracts*, vol. 122, #130053, 1996.

*Primary Examiner*—Thurman K. Page
*Assistant Examiner*—Sharon Howard
*Attorney, Agent, or Firm*—Lorusso & Loud

[57] ABSTRACT

A preparation is disclosed for producing enhanced blood flow in tissue thus causing beneficial effects such as warming cold tissue of the hands and feet. Specifically, this is a preparation which provides local delivery of the amino acid L-arginine, an important biological precursor to the main substance which is responsible for relaxation of blood vessels permitting enhancement of blood flow. In the preferred embodiments, the L-arginine is provided so that it can be topically applied to the cold tissue. The preparation also contains agents which aids in the transfer of L-arginine into the tissue. In the preferred embodiments this agent overcomes the resistance to transfer caused by the high charge density of L-arginine. In the preferred embodiments this means is high ionic strength created by addition of choline chloride, magnesium chloride and sodium chloride. This preparation, when topically applied to cold tissue, warming begins within about 10 to 45 minutes and is sustained for periods as long as about 2 to 18 hours.

9 Claims, No Drawings

TOPICAL DELIVERY OF L-ARGININE TO CAUSE TISSUE WARMING

BACKGROUND

1. Field of the Invention

This invention relates to topical application of a cream, gel, or other vehicle which contains substances such as L-arginine which delivers these substances into tissue for the purpose of producing beneficial effects such as warming of cold or cool tissues, growth of hair on the scalp, healing of leg ulcers secondary to diabetes or confinement to bed, as well as beneficial effects through restoration of natural mechanisms based on improvement of local blood supply.

2. Prior Art

Approaches to improving local blood flow have been many and consist of both systemic and topical approaches. Many beneficial effects could be obtained should improvement in local blood flow be achieved since impairment of local blood flow causes a variety of negative consequences. Among these are cold hands and feet, baldness, leg ulcers, certain forms of impotence, as well as a variety of other things. There have been several attempts to warm cold tissue including cold hands, fingers, feet and toes. Many persons suffer from cold hands, feet or other body parts. This is often caused by insufficient blood flow in the cold tissue. Previously cold hands or feet have been treated by wearing warm socks or gloves, sometimes even socks or gloves which are mechanically heated. The use of hot packs and glove or shoe inserts which generate heat through chemical reactions has also been a potential solution. These approaches have obvious disadvantages, for example, in maintaining finger dexterity. Certain liniments containing, such as capsicum have been suggested. More recently, topical creams containing nitroglycerine have been used. See H. Natsuda et al., *Ryumachi* 34, 849 (1994). While these medicaments have enjoyed some level of success, the effects are often extremely transient in nature. Nitroglycerine creams also have the significant disadvantage that nitroglycerine is a cardioactive drug, raising concerns of effects on the heart.

The fundamental basis for cold tissue of the hands, fingers, feet and toes as well as other cold tissue is insufficient blood flow to the. tissue. It has been suggested by some that the use of increased blood flow through relaxation of blood vessels, particularly small and very small vessels may be of use in warming cold tissue. However reasonable this suggestion, many attempts to demonstrate warming by use of agents which produce vasodilation and therefore increased blood flow have produced negative results. See N Dietz et al., *J Appl Physiol* 76, 2047 (1994); S Whitmore et al., *J Rheumatol* 22, 50 (1995); S Singh et al., *Eur J Clin Invest* 25, 182 (1995). The only report of modest temporary success involved the use of nitroglycerine. See H Natsuda et al., *Ryumachi* 34, 849 (1994). The oral administration of the nitric oxide precursors, such as L-arginine, to produce warming secondary to vasodilation has been suggested. And a variety of indirect and non-definitive experiments have been conducted. See M. Sonntag et al., *Pflugers Arch* 420, 194 (1992); A. Agostoi et al., *Int J Clin Lab Res* 21, 202 (1991). Thus, while the literature contains suggestions that vasodilation by administration of oral L-arginine, the precursor of nitric oxide (endothelium-dependent relaxing factor), no reports exist of success in producing an actual warming of tissue using this agent. In fact Dietz (see N Dietz et al., *J Appl Physiol* 76,2047 (1994)) concludes from his data that "These data suggest that NO (nitric oxide) does not play a major role in cutaneous vasodilation during body heating in humans." Further Singh (see S Singh et al., *Eur J of Clin Invest* 25, 182 (1995)) in a study of patients with Raynaud's phenomenon (severely cold hands and/or feet) concludes that L-arginine, administered orally, failed to cause vasodilation (and therefore warming) in patients with Raynaud's phenomenon.

Accordingly, several objects and advantages of the instant invention are to warm cold tissue in hands, feet or other tissue by increasing blood flow in the tissue means of enhancement of the body's natural mechanisms. It is further an object and advantage of the instant invention to prophylactically prevent tissue from becoming cold by use prior to entering into situations which induce cold hands and feet such as skiing or other winter outdoors activities.

SUMMARY OF THE INVENTION

It was discovered that topical application of a nitric oxide precursor, L-arginine, in its various forms contained in a variety of topical preparations, either by themselves or with other agents to aid in penetration, such as a high ionic strength environment, neutralization of its charge in a complex or by other means, or included in a liposome or other biological carrier, or with an added penetrating agent when administered to cold or cool tissue causes a substantial and prolonged warming effect in the tissue.

In one embodiment of the invention, a penetrating cream containing L-arginine at an effective concentration and a salt, such as sodium chloride, at a concentration sufficient to create a hostile biophysical environment for the L-arginine in the cream is applied to the cold or cool tissue and within about 20 minutes begins to exert a warming effect which is prolonged, often lasting from about 2–18 hours. In persons with very cold tissue (for example about 22° C.) this warming effect can have a magnitude of about 10° C. or more.

Consequently, with the discovery of the present invention, a means to warm cold and cool tissue, a problem shared by many, was developed for improving this uncomfortable and often painful problem in human.

In preferred embodiments, the delivery vehicle is a penetrating cream, the L-arginine is present as L-arginine hydrochloride in a concentration sufficient to produce the desired effect and the agent which creates the hostile biophysical environment is sodium chloride at a concentration sufficient to aid in tissue absorption.

These and other objects and features of the present invention will become apparent to those skilled in the art from reading the description of the invention, which follows.

DETAILED DESCRIPTION OF THE INVENTION

The preferred embodiment consists of a base cream with the properties of excellent absorption into the skin which also contains L-arginine hydrochloride (12.5% w/v), choline chloride (10% w/v), magnesium chloride (5% w/v) and sodium chloride (5% w/v). The components of the base cream may be those commonly found in hand creams, such as water, mineral oil, glyceryl stereate, squalene, propylene glycol stearate, wheat germ oil, glyceryl stearate, isopropyl myristate, steryl stearate, polysorbate 60, propylene glycol, oleic acid, tocopherol acetate, collagen, sorbitan stearate, vitamin A & D, triethanolamine, methylparaben, aloe vera extract, imidazolidinyl urea, propylparaben, and BHA. L-arginine hydrochloride is a precursor to the molecule, nitric oxide, NO, being transformed into NO and citruline by the enzyme nitric oxide synthetase. Nitric oxide is the substance that relaxes the blood vessels, allowing for increased blood flow. Choline chloride, magnesium chloride and sodium chloride provides a high ionic strength environment for the highly charged molecule, L-arginine. This high ionic strength environment is an example of a hostile biophysical environment for L-arginine. That is, the highly charged ionic strength is an unfavorable environment for the highly charged L-arginine making the L-arginine anxious to move to a more hospitable, less charged environment such as human tissue. The base cream containing L-arginine, choline chloride, magnesium chloride and sodium chloride is the agent which is applied to the hands and/or feet to produce to produce a warming effect in the tissue.

The cream acts effectively to warm cold tissue such as hands, fingers, feet, toes or other tissue when applied to the tissue and rubbed into the tissue to assure maximal absorption. The warming effect, caused by increased blood flow in the tissue is not instant but begins within about 5 to 20 minutes. The effect is long lasting. Often the tissue remains warm for more than about 2 to 18 hours.

Other Embodiments
Other Active Agents

While L-arginine hydrochloride is the preferred active agent because it is the agent in nature itself, it is non-toxic, is highly soluble and it is inexpensive, other agents could be used which are also precursors or donors of nitric oxide. These include D,L-arginine, L-arginine, alkyl (ethyl, methyl, propyl, isopropyl, butyl, isobutyl, t-butyl) esters of L-arginine and salts thereof. Pharmaceutically acceptable salts include hydrochloride, glutamate, butyrate, and glycolate.

In the case of an alternative active agent were used it would be simply substituted for L-arginine in a delivery preparation and the preparation used as in the case of the L-arginine preparation.
Other Means of Effecting or Improving Absorption A variety of means for effecting or improving absorption of the active agent can be envisioned. One principle behind the absorption of a highly charged molecule such as L-arginine into tissue is to either create a biophysically hostile environment in the delivery vehicle such that L-arginine would prefer to be in tissue, or to package L-arginine in such a way that it is carried into tissue or neutralize its charge by derivitization or forming a neutral salt. Examples of biophysically hostile environments, include but are not limited to; high ionic strength by the addition of ionic salts such as sodium chloride, magnesium chloride or choline chloride; high or low pH by adding pharmaceutically acceptable acids or bases; and highly hydrophobic environments by decreasing water content and increasing lipid, oil and/or wax content. Examples of packaging which would be carried into tissue includes liposomes or emulsions of collagen, collagen peptides or other components of skin or basement membrane. Examples of neutralization of charge include delivery of the active agent in the form or an ester or salt such as arginine glutamate which is electronically neutral. In each case of creating a hostile biophysical environment for the active agent, the agent was added to an appropriate preparation. In the case of creating a high ionic strength ions such as but not limited to sodium chloride, potassium chloride, choline chloride, magnesium chloride, lithium chloride, alone or in combination were added in high concentration. Other highly charged molecules such as polylysine, polyglutamine, polyaspartate or copolymers of such charged amino acids may be used to create the hostile biophysical environment. Alternatively a hostile biophysical environment may be created by placing the highly charged L-arginine in an hydrophobic, oily environment such as in an oil-based cream containing little or no water. Absorption may further be aided by combining the use of hostile biophysical environments with the use of penetrating agents such as oleoresin capsicum or molecules containing heterocyclic rings to which are attached hydrocarbon chains.

EXAMPLE

In this example a person (female, age 52) with very cold fingers was provided with the above warming cream consisting of a delivery vehicle of penetrating cream, L-arginine hydrochloride (12.5%), choline chloride (10%), magnesium chloride (5%) and sodium chloride (5%). The surface temperature of the subject fingers of the left hand varied from 21 to 24° C. The warming cream was applied through rubbing into the skin. Surface temperatures of each finger were measured each 15 minutes for the initial hour. At 15 minutes following administration of the warming cream the effect had begun to occur with surface temperatures or various fingers rising to 26 to 29° C. The maximal effect was reached by 45 minutes with surface temperatures of various fingers becoming 31 to 34° C. The effect was sustained at least 4 hours.

Accordingly, it can be seen that in the present invention I have provided agents, which when applied to cold, and often painful tissue, increase skin temperature through utilization of one of the body's own mechanisms for producing warmth occurs. This effect is achieved by providing the biochemical substrate at the local site from which nitric oxide is produced. Nitric oxide causes increased local blood flow, resulting in warming.

Although the description above contains many specificities, these should not be construed as limiting the scope of the invention but as merely providing illustrations of some of the presently preferred embodiments of this invention. Various other embodiments and ramifications are possible within this scope.

Thus the scope of the invention should be determined by the appended claims and their legal equivalents, rather than by the examples given.

What is claimed is:

1. A method of warming tissue comprising delivering a nitric oxide releasing substance selected from a member of the group consisting of L-arginine, L-arginine salts and L-arginine derivatives, to skin comprising the step of topically applying to the skin a vehicle containing an effective amount of the substance, and a concentration of ionic salt sufficient to create an ionic environment which causes the substance to migrate from the vehicle to the skin where the substance is absorbed.

2. The method of claim 1 wherein a topical delivery vehicle selected from the group consisting of topical creams, topical liquids, topical lotions and topical ointments containing the substance and the ionic salt is applied to the skin.

3. The method of claim 1 wherein a hydrophobic delivery vehicle containing the substance and the ionic salt is applied to the skin.

4. The method of claim 1 wherein a vehicle containing the substance and the ionic salt within a liposome, and the is applied to the skin.

5. The method of claim 1 wherein a vehicle containing the substance and the ionic salt within a liposome and an ionic salt concentration sufficient to create an ionic strength environment within the liposome is applied to the skin so that the liposomes migrate from the vehicle to the skin.

6. The method of claim 1 wherein a transdermal patch containing the substance and the ionic salt is applied to the skin.

7. The method of claim 1 wherein a delivery vehicle comprising water (20–80%), mineral oil (3–18%), glyceryl stearate (0.25–12%), squalene(0.25–12%), cetyl alcohol (0.1–11%), propylene glycol stearate (0.1–11%), wheat germ oil (0.1–6%), polysorbate 60 (0.1–5%), propylene glycol (0.05–5%), collagen (0.05–5%), sorbitan stearate (0.05–5%), vitamin A&D (0.02–4%), vitamin E (0.02–4%), triethanolamine (0.01–4%), methylparaben (0.01–4%), aloe vera extract (0.01–4%), imidazolidinyl urea (0.01–4%), propylparaben (0.01–4%), bha (0.01–4%), L-arginine hydrocholide (0.25% to 25%), sodium chloride (0.25% to 25%), the substance and the P depleting agent is applied to the skin.

8. The method of claim 7 wherein a delivery vehicle further comprising choline chloride (0.25–25%) is applied to the skin.

9. The method of claim 7 wherein a delivery vehicle further comprising L-arginine glumate (0.25–25%) is applied to the skin.

* * * * *